United States Patent [19]

Marmor et al.

[11] Patent Number: 5,597,924
[45] Date of Patent: Jan. 28, 1997

[54] COVERSION OF SUBSTITUTED 8-CHLOROQUINOLINES TO SUBSTITUTED 8-HYDROXYQUINOLINES

[75] Inventors: Robert S. Marmor, Princeton Junction; Henry L. Strong, Somerset, both of N.J.

[73] Assignee: American Cyanamid Company, Madison, N.J.

[21] Appl. No.: 448,693

[22] Filed: May 24, 1995

[51] Int. Cl.⁶ .................. C07D 215/18; C07D 215/26
[52] U.S. Cl. ............................................. 546/179; 546/180
[58] Field of Search ...................... 546/179, 180

[56] References Cited

U.S. PATENT DOCUMENTS

| | | | |
|---|---|---|---|
| 4,520,099 | 5/1985 | Akimura | 430/613 |
| 4,609,734 | 9/1986 | Quarroz | 546/290 |

FOREIGN PATENT DOCUMENTS

| | | |
|---|---|---|
| 3614756 | 11/1987 | Germany . |
| 48054078 | 8/1993 | Japan . |

OTHER PUBLICATIONS

Thomas Brown, "Reversible Inhibitors of the Gastric . . . ", J. Med. Chem, vol. 33, pp. 527–533, 1990.

Gerard Leclerc, "Cardiotonic Agents . . . ", J. Med. Chem., vol. 29, pp. 2433–2438, 1986.

Woroshzow; Mizengendler, Ah. Obshch. Khim., 6(1936)63. Conversion of unsubstituted 8-chloroquinoline to 8-hydroxyquinoline with cuprous salts in aqueous sodium hydroxide at 250 deg C.

Kawasaki, Shinjiro; Hirano, Akio; Hayashi, Yasuo (Taoka Dyestuffs Manufg. Co., Ltd.) Japan Kokai 73 54078, 30 Jul. 1973, Chem Abstr. 80, 37019 (1974).

Onishi, Isao; Agatsuma, Shigeru; Yamada, Hiroyuki; Yasuse, Shuichi; Murase, Yoshio (Yuki Gosei Kogyo Co., Ltd.) Japan Patent 47037436, 20 Sep. 1972, Chem Abstr. 78, 16059x (1972).

*Primary Examiner*—C. Warren Ivy
*Assistant Examiner*—D. Margaret M. Mach
*Attorney, Agent, or Firm*—Joseph M. Mazzarese

[57] ABSTRACT

The invention is a process for preparing substituted 8-hydroxyquinolines from substituted 8-chloroquinolines.

6 Claims, No Drawings

COVERSION OF SUBSTITUTED 8-CHLOROQUINOLINES TO SUBSTITUTED 8-HYDROXYQUINOLINES

SUMMARY OF THE INVENTION

The invention is a process for the conversion of substituted 8-chloroquinelines to substituted 8-hydroxyquinolines in the presence of a cupric catalyst. The compound 8-hydroxy-3-methoxymethylquinoline, a product of the process, is a precursor to the imidazolinone herbicide I.

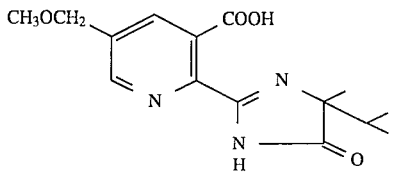

DETAILED DESCRIPTION

The invention is a pressure reactor process for preparing substituted 8-hydroxyquinolines as follows:

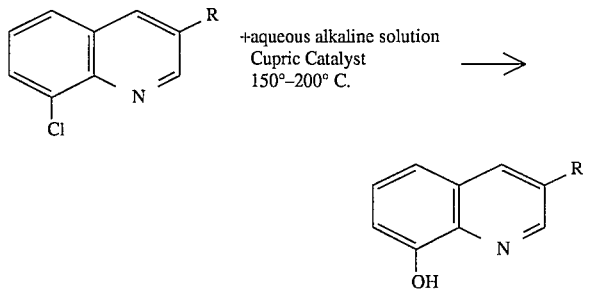

wherein R is $C_1$–$C_4$alkyl, hydroxy-$C_1$–$C_4$alkyl, $C_1$–$C_4$alkoxy-$C_1$–$C_4$alkyl, $C_1$–$C_4$haloalkyl, and di-$C_1$–$C_4$alkylamino-$C_1$–$C_4$alkyl.

The compound 8-hydroxy-3-methoxymethylquinoline, which may be prepared according to the process of the invention, is an intermediate in the synthesis of the imidazolinone herbicidal agent I as follows:

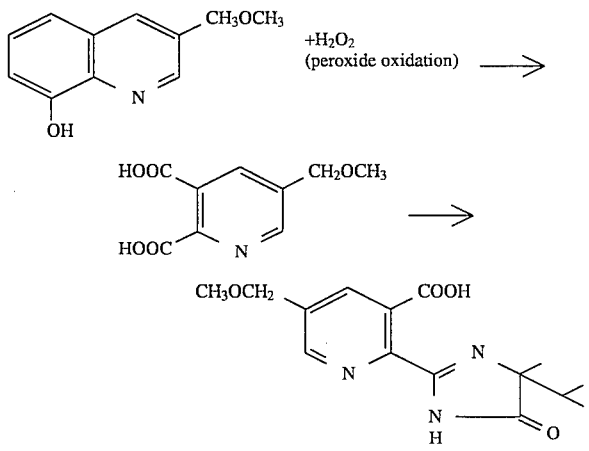

as taught in W. F. Reiker and W. A. Daniels U.S. Pat. No. 4,816,588 (1989) "Method for the Preparation of Pyridine-2,3-dicarboxylic Acids," and in Marinus Los U.S. Pat. No. 4,798,619 (1989) "2-(2-Imidazolin-2-yl) pyridines and -quinolines and Use of Said Compounds as Herbicidal Agents."

The following examples illustrate my invention but are not to be construed as a limitation thereto.

EXAMPLE 1

Into a tantalum liner in a 600 ml stirred Parr pressure reactor is placed 4.15 g 8-chloro-3-methoxymethylquinoline (20 mmol), 8.0 g 50% aqueous sodium hydroxide (100 mmol) and a solution of 250 mg cupric sulfate pentahydrate (1.0 mmol, 5 mole percent) in 95 ml of water. Sodium hydroxide concentration is 4%. The system is sealed, brought to 160 degrees C and held for 21.5 hours. The cooled solution is filtered through Celite, extracted with two 20 ml portions of toluene, then the aqueous layer is adjusted to pH 3–4 with sulfuric acid and finally to pH 7 with ammonium hydroxide. The mixture is extracted with two 50 ml portions of ethyl acetate. Rotary evaporation of the organic layer gives 2.39 g (63% yield) of crude 8-hydroxy-3-methoxymethylquinoline as a yellow green solid. The crude material is treated with two 500 ml portions of boiling water, leaving behind some insolubles. Long silky yellow needles of pure 8-hydroxy-3-methoxymethylquinoline separate. After filtering and drying, 1.83 g (48% yield) is obtained.

EXAMPLE 2

The Example 1 reaction is repeated in the same manner except 195 ml of water is used, thus the sodium hydroxide concentration is 2%. A similar workup affords 2.56 g (68% yield) of crude 8-hydroxy-3-methoxymethylquinoline. Recrystallization from hot water gives 1.92 g (51% yield) of pure material.

EXAMPLE 3

The Example 1 reaction is repeated on a larger scale with modified workup. Into a one gallon #316 stainless steel stirred Parr pressure reactor is placed 31.1 g 8-chloro-3-methoxymethylquinoline (150 mmol), 60 g 50% aqueous sodium hydroxide (750 mmol), and a solution of 1.87 g cupric sulfate pentahydrate (7.5 mmol, 5 mole percent) in 1460 ml of water. The system is sealed, brought to 160 degrees C and held for 17 hours. The cooled solution is filtered through Celite, then chilled thoroughly in an ice bath. The pH is adjusted to 4 with 50 ml concentrated hydrochloric acid, then to pH 8 with approximately 5 ml ammonium hydroxide. The resulting precipitate is filtered and washed with water. After drying overnight in a 60 degree C vacuum oven, 19.64 g of gray green powder, crude 8-hydroxy-3-methoxymethylquinoline (69% yield) is obtained. The filtrate is extracted with three 250 ml portions of ethyl acetate. Rotary evaporation of the organic layers gives 4.10 g of dark green oil, crude product (14% yield, thus total crude yield is 83%). Recrystallization of this oil from hot water affords 1.24 g of yellow-green needles of pure product.

EXAMPLE 4

A cupric complex of 8-hydroxy-3-methoxymethylquinoline is prepared by reacting one equivalent of cupric sulfate pentahydrate with two equivalents 8-hydroxy-3-methoxymethylquinoline in excess aqueous sodium hydroxide. The precipitated green powder is filtered, washed with water, and dried to constant weight. The Example 3 reaction is repeated, replacing the 1 mole percent cupric sulfate with 1.5 mole percent of the cupric complex of 8-hydroxy-3-methoxymethylquinoline. Similar workup gives an 80% yield of first crop product, and an additional 11% yield of second crop, thus overall crude yield is 91%.

EXAMPLE 5

The Example 4 reaction is repeated using 1.0 mole percent of the cupric complex of 8-hydroxy-3-methoxymethylquinoline. The overall crude yield is 92%. The product is purified by precipitation of the hydrochloride salt by addition of concentrated hydrochloric acid to a solution of the crude product in acetone. Overall yield of the hydrochloride salt is 58%.

EXAMPLE 6

The Example 5 reaction is repeated in an identical manner. The overall crude yield is 94%. Analyses of the product indicates a 78% real yield.

What is claimed is:

1. A process for preparing substituted 8-hydroxyquinolines which comprises reacting substituted 8-chloroquinoline of the formula

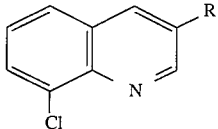

wherein R is $C_1$–$C_4$alkyl, hydroxy-$C_1$–$C_4$alkyl, $C_1$–$C_4$-alkoxy-$C_1$–$C_4$alkyl, $C_1$–$C_4$haloalkyl, and di-$C_1$–$C_4$alkylamino-$C_1$–$C_4$alkyl in a stirred pressure reactor with dilute alkaline solution in the presence of a cupric catalyst at a temperature within the range of about 150°–200° C.

2. A process according to claim 1 wherein the cupric catalyst is a cupric salt or an organic cupric complex and the alkaline solution is sodium hydroxide.

3. A process according to claim 2 wherein 8-chloro-3-methoxymethylquinoline is converted to 8-hydroxy-3-methoxymethylquinoline.

4. A process according to claim 3 wherein the catalyst is about 1 molar percent of the organic cupric complex prepared from the reaction of cupric sulfate and 8-hydroxy-3-methoxymethylquinoline, and the sodium hydroxide is about 5 equivalents 2% aqueous sodium hydroxide wherein the reaction is stirred for about 17 to about 24 hours at a temperature of about 160° C.

5. A process according to claim 3 wherein the catalyst is about 5 molar percent cupric sulfate and the sodium hydroxide is about 5 equivalents of about 2% to 4% aqueous sodium hydroxide wherein the reaction is stirred for about 17 to about 22 hours at a temperature of about 160° C.

6. A process according to claim 5 wherein the sodium hydroxide is about 5 equivalents of about 2% aqueous sodium hydroxide.

* * * * *